United States Patent [19]

Donahue

[11] Patent Number: 5,301,807
[45] Date of Patent: Apr. 12, 1994

[54] SURGICAL SCALPEL HOLDER

[76] Inventor: Deanna M. Donahue, 4696 Burch Creek Dr., Ogden, Utah 84403

[21] Appl. No.: 7,723

[22] Filed: Jan. 22, 1993

[51] Int. Cl.5 .......................................... B65D 83/10
[52] U.S. Cl. ................... 206/370; 206/363; 220/523; 220/553; 220/555
[58] Field of Search ............... 206/363, 364, 365, 366, 206/370; 220/4.21, 4.22, 337, 339, 523, 526, 553, 555

[56] References Cited

U.S. PATENT DOCUMENTS

| 722,943 | 3/1903 | Chappell | 206/365 |
|---|---|---|---|
| 746,999 | 12/1903 | Schmitz | 206/370 |
| 2,662,637 | 12/1953 | Armbruster | 206/370 |
| 3,135,456 | 6/1964 | Palazzolo | 220/4.22 |
| 3,380,573 | 4/1968 | Gulotta | 206/370 |
| 3,665,790 | 5/1972 | Jones | 220/555 |
| 3,937,389 | 2/1976 | Wind | 220/4.21 |
| 3,994,416 | 11/1976 | Mulligan | 220/338 |
| 4,133,449 | 1/1979 | Ostowsky | 220/339 |
| 4,349,120 | 9/1982 | DiNardo | 220/338 |
| 4,733,796 | 3/1988 | Halverstadt et al. | 220/339 |
| 5,046,624 | 9/1991 | Murphy et al. | 206/370 |
| 5,076,437 | 12/1991 | Schindler | 220/523 |
| 5,139,165 | 8/1992 | Hara | 220/339 |

Primary Examiner—David T. Fidei
Attorney, Agent, or Firm—A. Ray Osburn

[57] ABSTRACT

A holder used to provide scalpels for use during a surgical operation, and to dispose of scalpels after use. A number of scalpels are held in separated positions to be easily grasped when needed. The holder includes a cover for the blade ends of the scalpels, and a retractable cover for the handle ends. Each scalpel rests readily gripped on edge in its individual compartment. Adhesive pads-are optionally used to secure the holder in fixed location on an instrument tray during the operation.

15 Claims, 3 Drawing Sheets

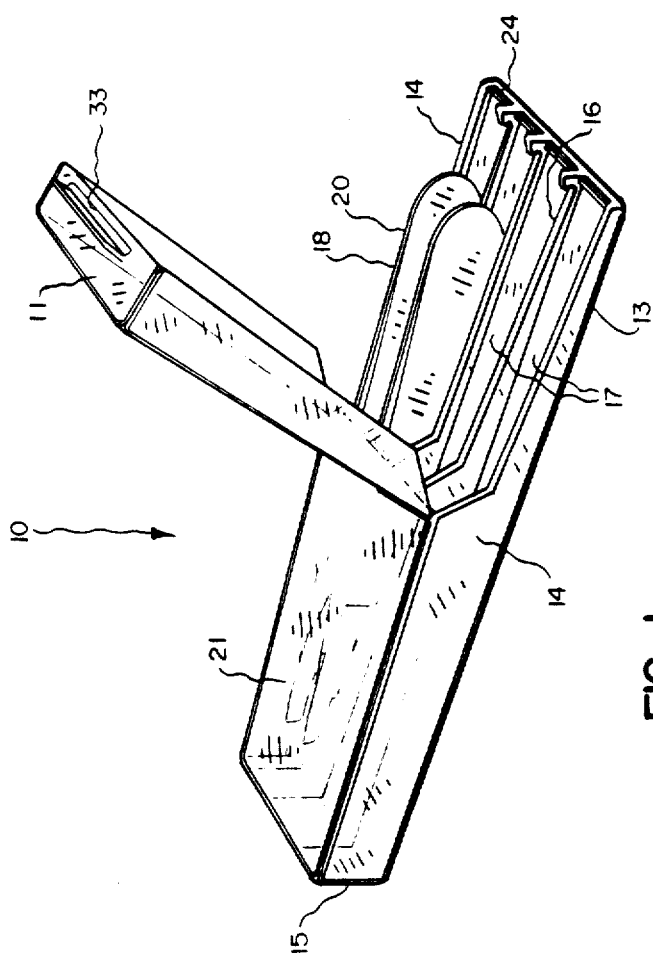
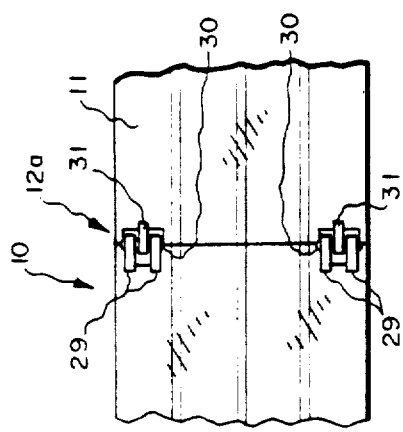
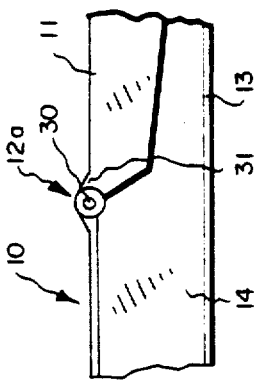
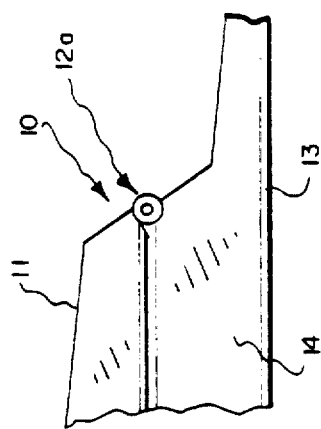
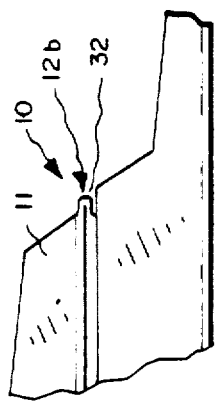
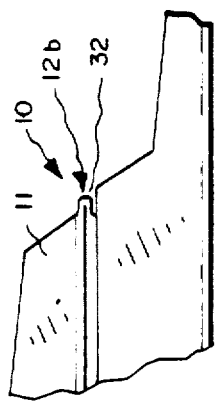

SURGICAL SCALPEL HOLDER

BACKGROUND OF THE INVENTION

Field

The field of the invention is surgical accessories, and more particularly devices for maintaining a group of scalpels safely and readily accessible during surgery.

State of the Art

Heretofore, scalpels used during surgery have been laid unrestrained directly upon the surface of instrument trays, generally separated for individual pickup by an attending nurse for handing to the surgeon. Accidental brushing or nudging not infrequently leads to disarray of the group of scalpels. The resulting difficulty in locating and identifying the needed scalpel leads to delays and potential error in selection. At times, the nurse may even be reduced to coping with a handful of loose scalpels before selection. Sometimes, nurses are accidentally cut by the extremely sharp blades during such handling. The problem is often acerbated when the scalpel handles are thin and wide, lying flatly upon the tray in difficult to grasp positions.

A need therefore exists for a device to hold scalpels in separated, accessible location and position, with the blades safely shielded until needed and again after use, to prevent accidents and to promote operation efficiency.

BRIEF SUMMARY OF THE INVENTION

With the foregoing in mind, the present invention eliminates or substantially alleviates the disadvantages of present methods of handling scalpels during and after surgery, by providing a holder having elongate compartments for the individual scalpels, formed by parallel walls upstanding from a flat base member. The portion of the compartments housing the blade end of the scalpels is covered for safety, while the handle housing portions open upwardly and have lowered walls exposing the handles for easy gripping. The compartments are preferably narrow enough to cause flat handled scalpels to rest on edge to be easily graspable.

Preferably, the scalpel case incorporates a hinged cover over the handle portion, the hinge perferably permitting fully 180° rotation. The opened cover may then rest upon the top of the blade housing portion, assuring an unobstructing low profile for the holder upon the instrument tray. Catch means may be provided to hold the cover in both closed and open positions.

The holder prevents jumbling and disarray of the scalpels whether or not provided with a cover, or whether or not anchored in fixed position upon the instrument tray. However, the holder preferably includes adhesive means on its bottom for optional anchoring, such as adhesive patchs covered by a nonadhering, strippable, coverings. When the holder is anchored, the surgical nurse may grasp and pass the scalpel to the surgeon and receive and replace it after use. When not anchored, the nurse may present the holder to the surgeon for directly selecting the scalpel and for directly replacing the scalpel into the holder after use.

With the secured cover, the holder containing used disposable scalpels may be directly discarded without further unsafe handling. With reusable scalpels, the holder provides safe transport to the sterilizing autoclave.

It is therefore the principal object of the invention to provide a scalpel holder which enhances the safety and efficiency of surgical operations. Another object is to provide safe handling of disposable and reusable scalpels after use.

BRIEF DESCRIPTION OF THE DRAWINGS

In the drawings, which respresent the best modes presently contemplated for carrying out the invention, FIG. 1 is a perspective view of a scalpel holder in accordance with the invention, with the handle cover thereof shown in the partially open position to expose scalpels in the individual compartments therefor, drawn to approximately full scale, FIG. 2 a top plan view of the scalpel holder of FIG. 1 with the handle cover thereof in closed position, taken along line 2—2 of FIG. 1, drawn to the same scale, FIG. 3 a side elevation view of the holder of FIG. 2, partially cut away to show the cover retaining catch, drawn to the same scale, FIG. 4 the scalpel holder of FIG. 3, shown with the handle cover in fully open position, drawn to the same scale, FIG. 5 an enlarged detail of the hinge connecting the cover to the holder of FIG. 3, drawn to an enlarged scale, FIG. 6 an enlarged detail of the cover retaining catch means of FIG. 3, drawn to an enlarged scale, FIG. 7 a top plan view of a fragment of a holder in accordance with the invention showing a pivot post and pin hinge, drawn to substantially full scale, FIG. 8 a side elevational view of the fragment of FIG. 7, drawn to the same scale, FIG. 9 a side elevation view of the fragment of FIG. 8, shown with the handle cover in open position, drawn to the same scale, FIG. 10 a side elevation view of a fragment of a scalpel holder in accordance with the invention showing a live hinge connecting the scalpel cover to the holder, drawn to the scale of FIG. 3, FIG. 11 the fragment of FIG. 10 with the scalpel handle cover shown in open position, drawn to the same scale, FIG. 12 a top plan view of a scalpel holder not having a blade shield plate nor a retractable scalpel handle cover, drawn to substantially full scale, FIG. 13 a top plan view of a scalpel holder in accordance with the invention, having rearwardly tapering scalpel holder compartments, shown without scalpel blade cover or retractable handle cover, drawn to substantially full scale, and FIG. 14 a front end sectional view of the scalpel holder of FIG. 1, showing scalpels in the compartments thereof disposed upon edge leaning against the walls of the compartments thereof, drawn to substantially full scale.

DETAILED DESCRIPTION OF ILLUSTRATED EMBODIMENTS

Figure 2:
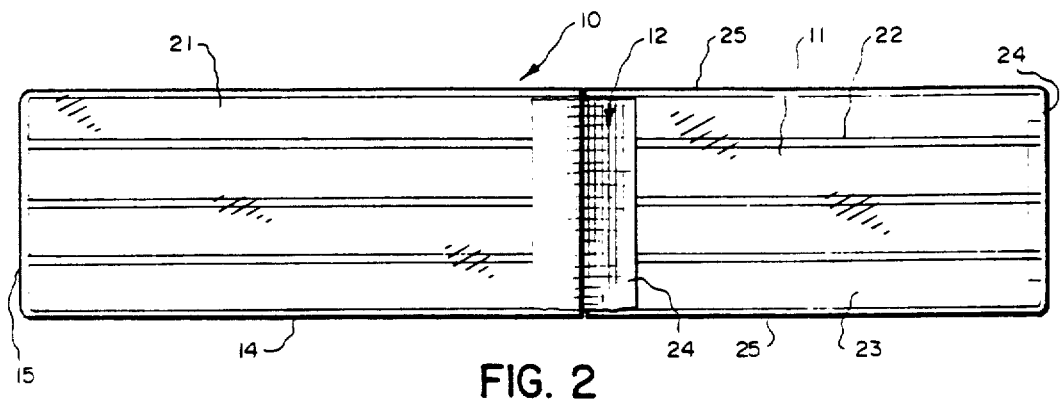
Figure 3:
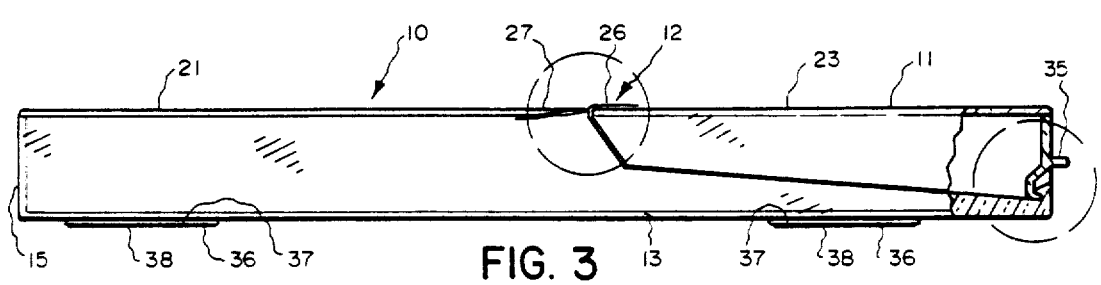

In FIG. 1, a scalpel holder 10 in accordance with the invention is shown in perspective with a cover assembly 11 partially rotated about a hinge 12. The scalpel holder 10 comprises a base plate 13 from which upstands a pair of sidewalls 14 joining a rearmost wall 15. Three interior partition walls 16 are spaced to form with the sidewalls four compartments 17 each sized to hold a single scalpel 18 with its blade end toward rear wall 15. The scalpel 18 typically comprise a thin blade member 19 secured to an also thin handle member 20. A blade shielding member 21 is affixed to sidewalls 14 and rear wall 15 to prevent any injurious blade contact. A retractable cover 22 over scalpel handles 20 closes holder 10. Upper plate 23 of cover 22 is joined to blade shield 21 by hinge 12.

Figure 14:
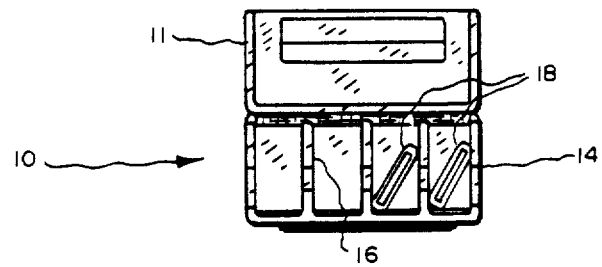

The compartments 17 are each narrow to assure that the scalpels stand on edge substantially vertically so that the handles 20 may be easily grasped. The the same time, the compartments are wide enough for finger room between the handles, again for easy grasping. The sidewalls and partition walls are high enough to accommodate the scalpel vertically on edge beneath blade shield 21. (FIG. 14) Compartments 17 which are ⅜" high and 5/16" wide have proven satisfactory. The sidewalls and the partition walls all lower abruptly forwardly of hinge 12, the handles 20 extending well above their upper edges. A low foremost wall 24 on base plate 13 may be provided to retain the scalpels in holder 10 in the event of tilting when cover 22 is open.

Figure 4:
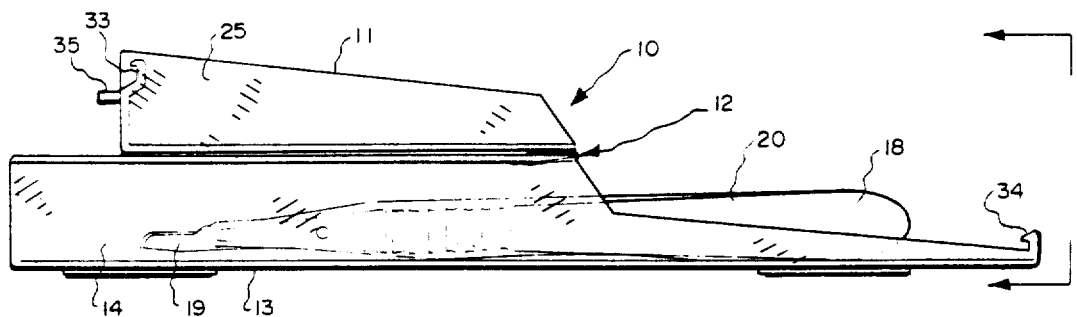
Figure 5:
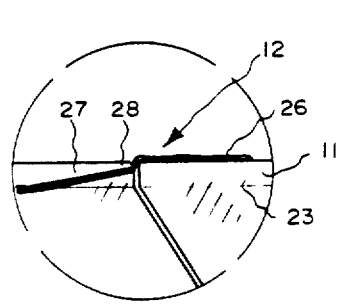
Figure 6:
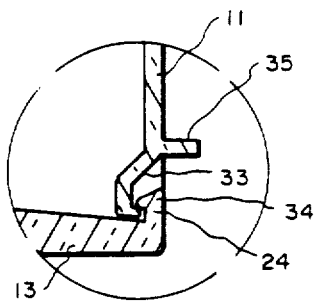

Cover 11 comprises the upper plate 23 and a pair of cover sidewalls 25 shaped to conform to the upper edges of the upstanding sidewalls 14. (FIGS. 2-6) When open, cover 11 is preferably rotated substantially 180° to rest against blade shield plate 21. FIGS. 4, 9 and 11. The resulting low profile minimizes instrument tray obstruction.

The hinge assembly 12 of FIGS. 2-6 comprises a thin flexible fabric member 26 adhered to the upper surface of cover upper plate 23 and to the under surface of blade shield plate 21. A tapered portion 27 provides a thin abutting edge 28 at the hinge axis, reducing slack in fabric 26 needed for clearance during rotation of cover 11.

The hinge assembly 12a of FIG. 7-9 comprises conventional pivot posts 29 on shield plate 21, linked by aligned pins 30 to posts 31 on cover 11. The common axis of pins 30 is preferably coplanar with the upper surface of shield plate 21, providing the desired 180° rotation of cover 11.

The hinge assembly 12b of FIGS. 10 and 11 utilizes a thin "live" hinge portion 32 molded integrally with shield plate 21 and cover upper plate 23. It is expected that catch means, not shown, would be required to retain cover 11 fully retracted, because live hinges are quite resilient.

A snap catch recess 33 in cover front wall 24 engages upstanding hooks 34 to hold cover 11 closed until released by lifting of tab 35.

To anchor holder 10 to the instrument tray, adhesive pads 36 are provided on the bottom of base plate 13. Upper adhesive layers 37 stick to base plate 13, and are covered by a strippable sheet 38. If holder 10 is utilized as an instrument passing tray, strip sheet 38 is left in place, rather than removed as when holder 10 is anchored.

Figure 12:
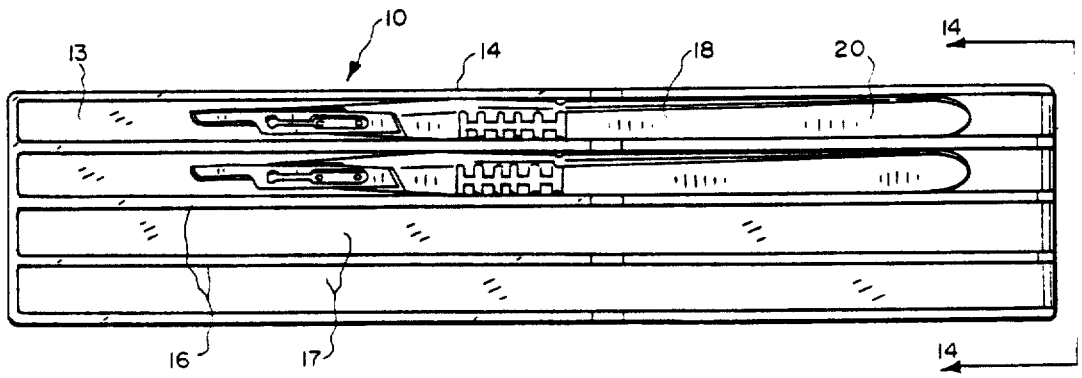
Figure 13:
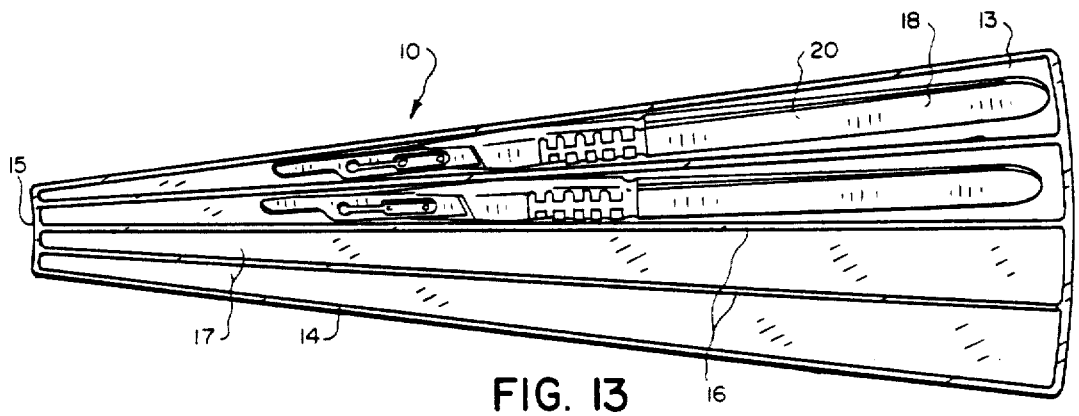

As described, the illustrated preferred embodiments of scalpel holder 10 permits its use anchored or as an instrument passing case, and serves also as a safe disposal container for used scalpels, or as a safely handled package of scalpels for sterilization preparatory for reuse. However, holder 10 would fulfill its primary objective of preventing scalpel disarray on the instrument tray without the retractable cover 11, and even without blade shield plate 21, albeit at a considerable sacrifice of safety. (FIG. 12) The illustrated lower sidewalls and partition walls could be entirely eliminated, although with impaired grip facilitating separation of the handles 20. Although illustrated as rectangular, holder 10 could be of other shapes such as the tapered embodiment in FIG. 13, splaying the scalpel handles further apart for easier gripping. Other changes are possible without departing from the spirit of the invention.

The invention may be embodied in still other specific forms without departing from the spirit or essential characteristics thereof. The present embodiments are, therefore, to be considered as illustrative and not restrictive, the scope of the invention being indicated by the appended claims rather than by the foregoing description, and all changes that come within the meaning and range of equivalency of the claims are, therefore, intended to be embraced therein

What is claimed and desired to be secured by United States Letters Patent is:

1. A scalpel holder to facilitate the conduct of a surgical operation, comprising:
   a horizontal, planar, base;
   a pair of spaced apart sidewalls upstanding from the base, each joining a rear wall upstanding from said base; and
   at least one elongate, interior partition wall upstanding from the base, forming together with the sidewalls at least two elongate scalpel holding compartments; wherein each compartment comprises
   an elongate rearward part proportioned so that the walls support a scalpel with a thin wide flat handle with an elongate edge resting upon the base, said walls being spaced sufficiently close together to hold the flats of said handle substantially vertical in easily graspable position; and wherein
   the base extends forwardly of the rearward part of the compartments sufficiently for the scalpel to rest full length thereon, and the rear wall and at least the sidewalls at the scalpel supporting rearward part of each compartment of the holder upstand a distance greater than the width of a flat handled scalpel to be held in the compartment; and wherein
   each wall portion forming the rearward part of each compartment is joined by a lowered wall portion forming a forward part of each compartment, said lowered wall portion having a height substantially less than the width of the scalpel handle, so that said lowered wall portion does not obstruct grasping of the handle.

2. The scalpel holder of claim 1, further comprising:
   a horizontal plate affixed at least to the sidewalls, said plate covering the rear, scalpel supporting, portions of the compartments, and having a foremost edge.

3. The scalpel holder of 2, further comprising:
   a removable cover over the forward portion of the holder, said cover having an uppermost, horizontal, member with a rearmost edge, said uppermost member carrying a pair of sidewalls downstanding therefrom and a front end wall downstanding therefrom, said cover being proportioned and sized to close the holder about the scalpels with said downstanding sidewalls respectively resting upon the lowered sidewall portions and with said uppermost horizontal member co-planar with said horizontal plate covering the rear portions of the compartments.

4. The scalpel holder of claim 3, wherein:

the removable covering means is connected by hinge means joining the rearmost edge of the uppermost flat plate thereof to the foremost edge of the rear compartment covering plate; and releasable means securing the covering means against rotation about the hinge means from the closed position.

5. The scalpel holder of claim 1 further comprising:
adhesive means for optionally securing the holder to an operating instrument tray.

6. The scalpel holder of claim 1, further comprising:
adhesive means for optionally securing the holder to an operating instrument tray.

7. The scalpel holder of claim 2, further comprising:
adhesive means for optionally securing the holder to an operating instrument tray.

8. The scalpel holder of claim 4, further comprising:
adhesive means for optionally securing the holder to an operating instrument tray.

9. The scalpel holder of claim 1 wherein:
the sidewalls and partition walls are parallel, so that the compartments are rectangular.

10. The scalpel holder of claim 2, wherein:
the sidewalls and partition walls are parallel, so that the compartments are rectangular.

11. The scalpel holder of claim 4, wherein:
the sidewalls and partition walls are parallel, so that the compartments are rectangular.

12. The scalpel holder of claim 8, wherein:
the sidewalls and partition walls are parallel, so that the compartments are rectangular.

13. The scalpel holder of claim 11, wherein:
the rear scalpel supporting portions of the compartments are §" in height by 5/16" in width.

14. The scalpel holder of claim 1 wherein:
the sidewalls and partition walls converge rearwardly, so that the compartments taper horizontally in the rearward direction and the handle ends of the scalpels are splayed apart to facilitate grasping said handle ends.

15. The scalpel holder of claim 4, wherein:
the sidewalls and partition walls converge rearwardly, so that the compartments taper horizontally in the rearward direction and the handle ends of the scalpels being held are splayed apart to facilitate grasping thereof.

* * * * *